United States Patent [19]

Bonin et al.

[11] Patent Number: 4,920,231
[45] Date of Patent: Apr. 24, 1990

[54] PROCESS OF BRAKING TRIFLOUROMETHYL COMPOUNDS

[75] Inventors: Werner Bonin, Kelkheim; Jean-Pierre Demoute, Neuilly Plaisance; Jean Tessier, Vincennes, all of France

[73] Assignee: Roussel Uclaf, Paris, France

[21] Appl. No.: 331,732

[22] Filed: Mar. 30, 1989

[30] Foreign Application Priority Data

Mar. 31, 1988 [FR] France ............................. 88 04260

[51] Int. Cl.⁵ ............................................. C07D 213/55
[52] U.S. Cl. ..................................... 546/300; 546/301; 548/127; 548/128; 548/129; 548/134; 548/135; 548/136; 548/142; 548/202; 548/204; 548/213; 548/214; 548/319; 548/477; 548/479; 549/417; 549/474; 549/475; 549/478; 556/442; 558/357; 558/407; 558/432; 558/434; 560/124
[58] Field of Search .............. 546/300, 301; 548/127, 548/128, 129, 134, 135, 136, 142, 202, 204, 213, 214, 319, 477, 479; 549/417, 474, 475, 478; 556/442; 558/357, 407, 432, 434; 560/124

[56] References Cited

U.S. PATENT DOCUMENTS 4,485,252 11/1984 Fuchs et al. ............................. 560/8
4,491,585 1/1985 Fuchs et al. ........................ 514/345

Primary Examiner—Richard A. Schwartz
Assistant Examiner—Richard A. Sharpe
Attorney, Agent, or Firm—Bierman and Muserlian

[57] ABSTRACT

A process for the preparation of trifluoromethylvinyl compounds in all their possible streoisomeric forms and mixtures thereof comprising reacting a salt of trifluoroacetic acid with a halovinyl compound in the presence of a cuprous salt to obtain the same stereo-specific compound and all possible stereo-isomeric forms and mixtures thereof of 1R, trans compounds of the formula

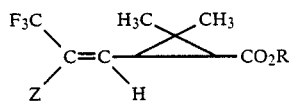

wherein R is an alcohol residue used in pyrethrinoid series, or an alcohol residue capable of blocking the acid function, and Z is aryl or haloaryl and the double bond has Z geometry having pesticide activity.

13 Claims, No Drawings

PROCESS OF BRAKING TRIFLOUROMETHYL COMPOUNDS

STATE OF THE ART

Related prior art compounds are disclosed in British Pat. No. 2,034,700, U.S. Pat. Nos. 4,737,513; No. 4,551,281; No. 4,344,963; No. 4,485,252; No. 4,491,585; No. 4,582,921 and No. 4,650,887 and Chemistry Letters, No. 12, Dec. 1981, pp. 1719–20.

OBJECTS OF THE INVENTION

It is an object of the invention to provide a novel process for preparing trifluorovinyl compounds from the corresponding halovinyl compounds.

It is another object of the invention to provide the novel cyclopropane carboxylates of formula I.

It is a further object of the invention to provide novel pesticidal compositions and a novel method of combatting pests.

These and other objects and advantages of the invention will be obvious from the following detailed description.

THE INVENTION

The novel process of the invention for the preparation of trifluoromethylvinyl compounds in all their possible stereoisomeric forms and mixtures thereof comprises reacting a salt of trifluoroacetic acid with a halovinyl compound in the presence of a cuprous salt to obtain the same stereo-specific trifluoromethylvinyl compound.

The process of the invention has the advantage of preserving the stereo-specificity of the halovinyl starting products. If the geometry of the double bond of the halovinyl product used is E, the geometry of the trifluoromethyl product is E and if the geometry of the double bond of the halovinyl product is Z, the geometry of the trifluoromethylvinyl product is Z. Preferably, the trifluoroacetic acid salt used is sodium trifluoroacetate and the cuprous salt used is cuprous iodide.

The process of the invention allows the preparation of numerous trifluoromethylvinyl products and especially certain derivatives of 2,2-dimethyl-cyclopropane carboxylic acid.

More particularly, the subject of the invention is a process for the preparation of the products of formula I

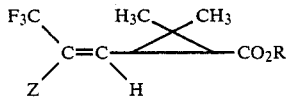

I in all their possible stereoisomeric forms and mixtures thereof wherein R is an alcohol residue used in pyrethrinoid series, or an alcohol residue capable of blocking the acid function, and Z is an electro-attracting group characterized in that a product of the formula

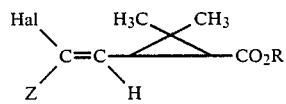

II in all their possible stereoisomeric forms and mixtures thereof wherein Z and R have the above meaning and Hal is bromine, chlorine or iodine is reacted with sodium trifluoroacetate in the presence of cuprous iodide to obtain the corresponding product of formula I.

The process is totally stereospecific with the geometry of the double bond and the structure of the cyclopropane moiety of the products obtained being the same as the starting products.

In a preferred method, Hal is bromine and more particularly, Z is aryl optionally substituted by a halogen such as, for example, phenyl substituted by a 4-chlorine.

In another preferred embodiment, Z is —COOR' and R' is alkyl of 1 to 8 carbon atoms. Examples of R' are methyl, ethyl, n-propyl and isopropyl. In a further preferred embodiment, R is alkyl of 1 to 8 carbon atoms optionally substituted with trialkylsilyl, preferably alkyl of 1 to 4 carbon atoms substituted with trimethylsilyl or benzyl optionally substituted with at least one member of the group consisting of alkyl of 1 to 4 carbon atoms, alkenyl and alkenyloxy of 2 to 6 carbon atoms, alkadienyl of 4 to 8 carbon atoms, halogen and methylenedioxy.

R may also be (a) a group of the formula

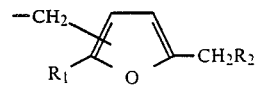

wherein $R_1$ is hydrogen or methyl and $R_2$ is monocyclic aryl or —C≡CH, (b) or a group

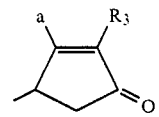

in which a is hydrogen or methyl and $R_3$ is an aliphatic organic of 2 to 6 carbon atoms having one or more carbon-carbon unsaturations, especially —CH$_2$—CH=CH$_2$, —CH$_2$C≡CH, —CH$_2$CH=CH—CH$_3$, —CH$_2$—CH=CH—CH=CH$_2$, or —CH$_2$—CH=CH—CH$_2$—CH$_3$, (c) or a group

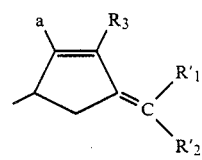

in which a is hydrogen or methyl, $R_3$ has the above definition, $R_1'$ and $R_2'$ are individually hydrogen, halogen, alkyl of 1 to 6 carbon atoms, aryl of 6 to 10 carbon atoms, alkoxycarbonyl of 2 to 5 carbon atoms, or cyano, (d) or a group

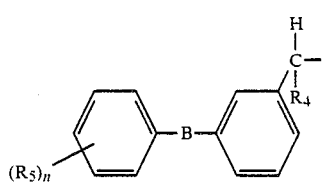

in which B is oxygen or sulfur,

or —CH$_2$— or a sulfoxide or a sulfone and R$_4$ is hydrogen, —C≡N, methyl, —CONH$_2$, —CSNH$_2$ or —C≡CH, R$_5$ is halogen or methyl and n is 0, 1 or 2, (e) or a group

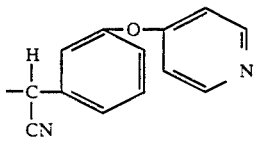

(f) or a group

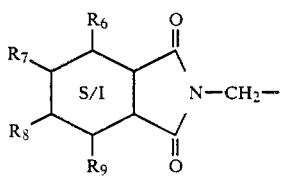

in which R$_6$, R$_7$, R$_8$, R$_9$ are hydrogen, chlorine, or methyl and which S/I symbolizes an aromatic ring or a dihydro or tetrahydro ring, (g) or a group

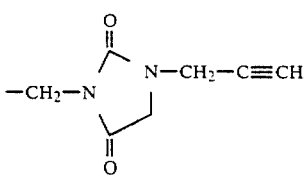

(h) or a group

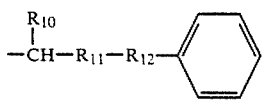

in which R$_{10}$ is hydrogen or —CN, R$_{12}$ is —CH$_2$— or oxygen, R$_{11}$ is thiazolediyl or thiadiazolediyl in which the bond with can be found in any of the positions available, R$_{12}$ is linked to R$_{11}$ by the carbon contained between the sulfur atom and the nitrogen, (i) or a group

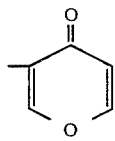

(j) or a group

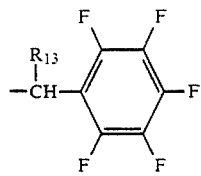

in which R$_{13}$ is hydrogen or —CN, (k) or a group

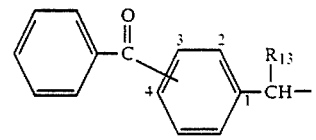

in which R$_{13}$ is defined as above, and the benzoyl radical is in position 3 or 4, (l) or a group

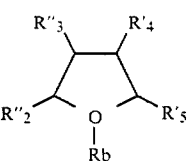

in which one of R$_2''$ or R$_3''$ is

Z is hydrogen, —C≡N, —C≡CH, —CF$_3$ or alkyl of 1 to 3 carbon atoms and the other R$_2''$ or R$_3''$ and R$_4'$ and R$_5'$ are individually hydrogen, halogen, alkyl of 1 to 18 carbon atoms, aryl of 6 to 14 carbon atoms, arylalkyl of 7 to 18 carbon atoms, cyano, —CF$_3$, alkoxycarbonyl of 2 to 8 carbon atoms, NO$_2$, alkyloxy of 1 to 8 carbon atoms,

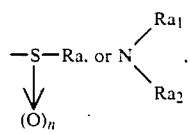

n being 0, 1 or 2 and the radicals Ra, Ra$_1$ and Ra$_2$ are alkyl of 1 to 8 carbon atoms, Rb is either

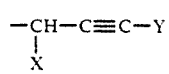

in which X and Y are individually hydrogen, halogen, alkyl of 1 to 8 carbon atoms or aryl of 6 to 14 carbon atoms or

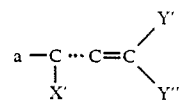

radical in which X', Y' and Y'' are individually one of the values indicated above for X and Y, the dotted line representing a possible double bond between the carbons 1 and 2;

(m) or

in which r' can have the values indicated previously for $R_4''$ and $R_5''$ with the exception of halogen, cyano, $-NO_2$,

in which n is either 1 or 2 and

(n) or

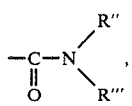

in which R'' and R''' are individually hydrogen, alkyl of 1 to 18 carbon atoms, aryl of 6 to 14 carbon atoms, aralkyl of 7 to 18 carbon atoms, $-CF_3$, alkoxycarbonyl of 2 to 8 carbon atoms or alkoxy of 1 to 8 carbon atoms, (o) or a group

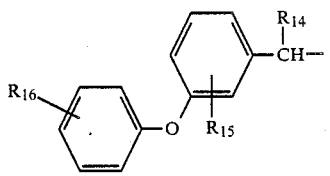

in which $R_{14}$ is hydrogen, methyl, ethynyl or cyano and $R_{15}$ and $R_{16}$ are individually hydrogen, fluorine or bromine, (p) or a group

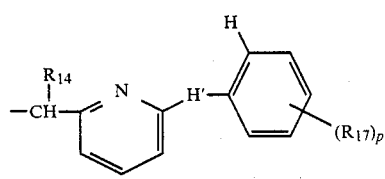

in which $R_{14}$ is defined as above, each of the $R_{17}$'s independently is alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo, p is an integer 0, 1 or 2 and B' is oxygen or sulfur.

The process of the invention permits the preparation of products, which are very useful as pesticides, as well as intermediates useful in the synthesis of these products such as certain products of the European Pat. No. 0,019,787. It also allows the preparation of new products and a subject of the invention is also these new products, namely methyl [1R-(1α, 3β)] 2,2-dimethyl-3-[(ΔZ)-2-(4-chlorophenyl)-3,3,3-trifluoro-1-propenyl]-cyclopropane carboxylate and 2-(trimethylsilyl) ethyl [1R-(1α, 3β)]2,2-dimethyl-3-[(ΔZ)-2-(4-chlorophenyl)-3,3,3-trifluoro-1-propenyl]-cyclopropane carboxylate.

Also an object of the invention are the products of the formula

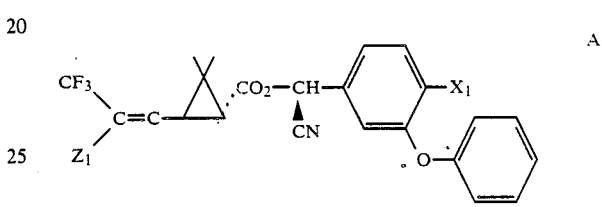

in which the cyclopropane moiety is of 1R trans structure, the geometry of the double bond is Z, $Z_1$ is aryl or alkyl substituted by a halogen, and X is hydrogen, or fluorine, and notably the product of the structure

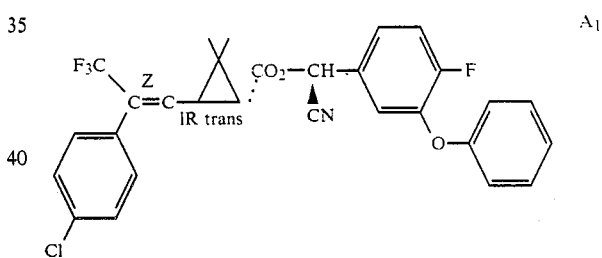

Also the products of formula I in all their possible stereoisomeric forms and mixtures thereof of the formula

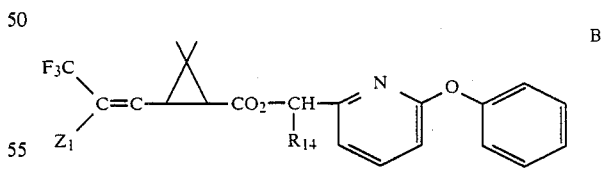

in which $Z_1$ and $R_{14}$ have the same meaning as previously, and especially those in which $R_{14}$ is methyl, or those in which $Z_1$ is

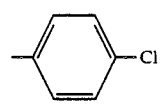

and especially the products of the formula $B_1$:

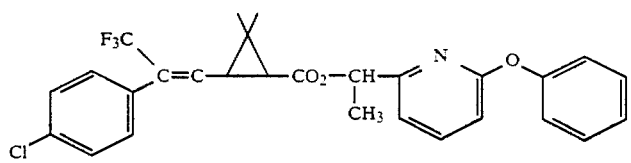

in all their possible stereoisomeric forms as well as mixtures thereof.

As indicated several times, one of the advantages of the process of the invention is that it is stereospecific, especially for the compounds in which the cyclopropane moiety is of 1R, trans structure and the geometry of the double bond is Z.

The novel pesticidal composition of the invention are comprised of a pesticidally effective amount of at least one compound of formula I and an inert carrier. The compositions are useful to combat pests such as parasites of vegetables and of warm-blooded animals such as cattle, sheep and fowl as well as parasites of premises and are particularly useful to combat insects, nematodes and parasitic acariens which attack warm-blooded animals and vegetables.

The compositions of the invention are particularly useful to combat insects in the agricultural field, for example, to control aphides and larvae of lepidoptera and coleoptera and are usually used at a dose of 10 to 300 g of the compounds of formula I per hectare. The compositions are also useful to combat insects in the premises for example to combat flies, mosquitoes and beetles. The insecticidal compositions of the invention are particularly preferred and may contain 0.005 to 10% by weight of the active ingredient.

In the advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 95% by weight, preferably.

In the case of a serpentine insecticide, the inert support may be made, for example, of pyrethrum marc, Tabu powder (or Machilus Thumbergii leaf powder), powder of pyrethrum stems, cedar needle powder, sawdust such as pine sawdust, starch and powder of coconut shells. The active dose in this case is preferably 0.03 to 1% by weight.

The compositions of the invention for premise use may be prepared as a spraying oil containing the active ingredient and the oil may soak the wick of a lamp which is then subjected to combustion. The concentration of the active compound in the oil is preferably 0.03 to 95% by weight.

The compositions of the invention are also useful to combat acariens and nematode parasites of vegetables containing at least one compound of formula A as the active ingredient and they may be in the form of powders, granules, suspensions, emulsions or solutions.

For acaricide use, the compositions are preferably wettable powders for foliar spraying containing 1 to 80% of the active ingredient or liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

The compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be liquid such as water, alcohol, hydrocarbons or other organic solvents or a mineral, animal or vegetable oil or a powder such as talc, clays, silicates or Kieselguhr or a combustible solid.

The compositions of the invention are also useful to combat acarien parasites of warm-blooded animals such as ticks, especially ticks of Boophilus species, Hyalomnia species, Amblyomnia species and Rhipicephalus species and to combat all sorts of scabies such as sarcoptic scabies, psoroptic scabies and chorioptic scabies. They can also be useful to combat lice and helminthes. The invention also includes compositions intended to combat parasites of warm-blooded animals, especially ticks and gales, containing at least one compound of formula I.

The said compounds may be administered externally by vaporization, by shampooing, by painting or by bathing. For veterinary usage, the compositions may also be administered by painting the dorsal spine by the "pour on" method. When the "pour on" method is used, it is preferred to use solutions containing from 0.5 to 5 g of active material per 100 ml of solution.

When the compositions are to be used to combat parasitic acariens of animals, the active compounds of formula I are very often incorporated into alimentary compositions in association with a nutritive mixture adapted to the animal to be fed. The nutritive mixture will vary depending upon the species of animal but usually contains cereals, sugars and grains, soybean press cake, peanuts and turnsole press cake, meal of animal origin such as fish meal, synthetic amino acids, mineral salts, vitamins and antioxidants.

Another feature of the invention are insecticidal, acaricidal or nemataocidal compositions containing as an active ingredient at least one compound of formula I and as a second active ingredient at least one pyrethrinoid ester selected from the group consisting of esters of allethrolone, of 3,4,5,6-tetrahydrophthalimidomethyl alcohol, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-caraboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxy-benzyl alcohol with 2-p-chloro-phenyl-2-isopropyl-acetic acids, esters of allethrolone, 3,4,5,6-tetraphthalimido-methyl alcohol, 5-benzyl-3-furyl-methyl alcohols, 3-phenoxy-benzyl alcohol or α-cyano-3-phenoxybenzyl alcohols with 2,2-dimethyl-3-(1,2,2,2-tetrahaloethyl)-cyclopropane-1-carboxylic acids where halo is fluorine, chlorine or bromine wherein the compounds of formula I and the above pyrethrinoid esters are in all possible stereoisomeric forms.

To increase the biological activity of the compositions of the invention, classical synergists may be incorporated therein such as 1-(2,5,8-trioxadodecyl)-2-propyl-4,5-methylenedioxy-benzene (piperonyl butoxide) or N-(2-ethyl-heptyl)-bicyclo-[2,2-1]-5-heptene-2,3-dicarboximide or piperonyl-bis-2-(2'-n-butoxy-ethoxy)-ethyl acetal (tropital).

The novel method of the invention for combatting parasites such as insects, nematodes and acariens comprises contacting the parasites with a pesticidally effective amount of at least one compound of formula A.

In the following examples there are described several preferred embodiments to illustrate the invention. However, it is to be understood that the invention is not intended to be limited to the specific embodiments.

EXAMPLE 1

Methyl [1R-(1α,3β)]-2,2-dimethyl-3-[(ΔZ)-2-(4-chlorophenyl-3,3,3-trifluoro-1-propenyl]-cyclopropane carboxylate

STEP A: Methyl [1R-(1α, 3β)]-2,2-dimethyl-3-[(ΔZ)-2-bromo-2-(4-chlorophenyl)-ethenyl] cyclopropane carboxylate and its 1R-[1α, 3β(ΔE)] isomer 7.8 g of methyl (1R, trans) 3-formyl-2,2-dimethyl-cyclopropane carboxylate and 17.7 g of dimethyl [bromo-(4-chlorophenyl)-methyl]-phosphonate were dissolved in 70 ml of tetrahydrofuran and after cooling to −40° C., over 45 minutes a solution of 6.16 g of potassium tert-butylate in 60 ml of tetrahydrofuran was added. The solution was stirred for 1 hour at −40° C. to −45° C. and then poured into a saturated aqueous solution of sodium acid phosphate, extracted with isopropyl ether, washed, dried and evaporated to dryness to obtain 18.7 g of the product which was chromatographed on silica and eluted with a mixture of hexane-isopropyl ether (95–5) to obtain 2.97 g of isomer Z (17%). 5.91 g of isomers (E) was also obtained (34.5%).

| NMR Spectrum CDCl$_3$ 60 MHz: | |
|---|---|
| (isomere Z) | |
| aromatic protons | 7.16 to 7.68 ppm |
| vinyl protons | 5.87 to 6 ppm |
| twinned methyl protons | 1.23 to 1.35 ppm |
| CO$_2$—CH$_3$ protons | 3.7 ppm |
| protons in position 1 of cyclopropane | 1.63 to 1.73 ppm |
| protons in position 3 of cyclopropane | 2.35 to 2.56 ppm |
| (isomere E) | |
| aromatic protons | 7.32 ppm |
| vinyl protons | 5.85 to 5.98 ppm |
| twinned methyl protons | 1.17 to 1.22 ppm |
| protons in position 1 of cyclopropane | 1.52 ppm |
| protons in position 3 of cyclopropane | 1.87 to 2.1 ppm |

STEP B: Methyl [1R-(1α, 3β)]2,2-dimethyl-3-[ΔZ)-2-(4-chlorophenyl)-3,3,3-trifluoro-1-propenyl]-cyclopropane caraboxylate 2.95 g of methyl [1R-(1α, 3β)] 2,2-dimethyl-3-[(ΔZ)-2-bromo-2-(4-chlorophenyl)-ethenyl]-cyclopropane carboxylate and 4.68 g of sodium trifluoroacetate were dissolved in 30 ml of N-methyl-pyrrolidone and 3.27 g of copper iodide were added. The mixture was heated at approximately 160° C. for 6 hours, allowed to return to ambient temperature, filtered, rinsed and distilled. The residue was extracted with isopropyl ether and the organic phase was then washed, dried and evaporated to dryness to obtain 3.94 g of product which was chromatographed on silica and eluted by an hexane-isopropyl ether mixture 95–5 to obtain 2.22 g of the desired product.

| NMR Spectrum CDCl$_3$ ppm: | |
|---|---|
| twinned methyl proton | 1.25 to 1.35 ppm |
| aromatic protons | 7.13 to 7.5 ppm |
| ethylenic protons | 5.63 to 5.80 ppm |
| carbon protons in position 3 of cyclopropane | 2.33 to 2.75 ppm |
| carbon protons in position 1 of cyclopropane | 1.69 to 1.78 ppm |
| CO$_2$—CH$_3$ protons | 3.75 ppm |

EXAMPLE 2

2-trimethylsilylethyl [1R-(1α, 3β)] 2,2-dimethyl-3-(ΔZ) 2-(4-chlorophenyl)-3,3,3-trifluoro-1-propenyl]-cyclopropane carboxylate

STEP A: 2-(trimethylsily) ethyl [1R-(1α, 3β)]2,2-dimethyl-3-[(ΔZ)-2-bromo-2-(4-chlorophenyl)-ethenyl] cyclopropane carboxylate and its corresponding E isomer 2.84 g of (1R trans) 2,2-dimethyl-3-formyl-cyclopropane carboxylic acid and 7.5 g of dimethyl [bromo-(4-chlorophenyl)-methyl]-phosphonate were dissolved in 20 ml of tetrahydrofuran and after the solution was cooled to −40° to −45° C., a solution of 5 g of potassium tert-butylate in 25 ml of tetrahydrofuran was added over 25 minutes. The solution was stirred for one hour at −40° to −45° C., then poured into a saturated aqueous solution of sodium acid phosphate and extracted with isopropyl ether. The extracts were washed, dried and evaporated to dryness to obtain 7.3 g of residue which was dissolved in 20 ml of methylen chloride.

2.85 ml of trimethylsilyl ethanol were added followed by about 4.53 g of dicyclohexylcarbodiimide at 0° C., followed by 70 mg of 4-dimethylamino pyridine and 15 ml of methylene chloride. Stirring was carried out for 5 minutes in an ice bath and then for one hour at ambient temperature. The mixture was filtered, rinsed with isopropyl ether and evaporated to dryness to obtain 9 g of product which was chromatographed with a hexane-isopropyl ether mixture (95–5) to obtain 3.11 g of the desired Z isomer.

| NMR Spectrum CDCl$_3$ ppm: | |
|---|---|
| aromatic protons | 7.15 to 7.52 ppm |
| protons of twinned methyls | 1.24 to 1.37 ppm |
| vinyl proton | 5.87 to 6 ppm |
| protons of the carbon in position 3 of the cyclopropane | 2.33 to 2.55 ppm |
| protons of the carbon in position 1 of the cyclopropane | 1.60 to 1.7 ppm |

-continued

NMR Spectrum CDCl₃ ppm:

| | |
|---|---|
| protons α to the C—O (C=O) | 4.05 to 4.33 ppm |
| protons β to the C—O (C=O) | 0.86 to 1.15 ppm |

1.88 g of E isomer were also obtained.

| | |
|---|---|
| aromatic protons | 7.32 ppm |
| protons of twinned methyls | 1.17 to 1.22 ppm |
| vinyl proton | 5.87 to 6 ppm |
| protons of the carbon in position 3 of the cyclopropane | 1.85 to 2.08 ppm |
| protons of the carbon in position 1 of the cyclopropane | 1.47 to 1.57 ppm |
| protons α to the C—O (C=O) | 3.96 to 4.25 ppm |
| protons β to the C—O (C=O) | 0.8 to 1.08 ppm |

STEP B: 2-(trimethylsilyl)-ethyl [1R-(1α, 3β)]-2,2-dimethyl-3-[(ΔZ)-2-(4-chlorophenyl)-3,3,3-trifluoro-1-propenyl]-cyclopropane carboxylate 3.06 g of the product of Step A and 3.86 g of sodium trifluoroacetate were dissolved in 30 ml of N-methyl pyrrolidone and 2.7 g of copper iodide were added. The reaction mixture was held at 160° C. for 6 hours, then allowed to return to ambient temperature, filtered, rinsed and the impurities were eliminated. After extracting with isopropyl ether, the extracts were diluted with hexane, washed with a saturated solution of sodium chloride, dried on sodium sulfate and evaporated to dryness to obtain 3.3 g of product which was chromatographed on silica and eluted with a hexane-toluene mixture 6–4 to obtain 1.69 g of the desired product which was re-chromatographed and eluted with a hexane-isopropyl ether mixture (95–5) to obtain 1.35 g of the expected product.

NMR Spectrum CDCl₃ ppm:

| | |
|---|---|
| aromatic protons | 7.08 to 7.42 ppm |
| vinyl protons | 5.62 to 5.8 ppm |
| twinned methyl protons | 1.22 to 1.32 ppm |
| carbon protons in position 1 of cyclopropane | 1.62 to 1.72 ppm |
| carbon protons in position 3 of cyclopropane | 2.35 to 2.82 ppm |
| protons α of the CO₂ | 4.05 to 4.33 ppm |
| protons β of CO₂ | 0.86 to 1.13 ppm |

EXAMPLE 3

1-(6-phenoxy-2-pyridyl)-ethyl [1R-[1α(R*), 3β]]2,2-dimethyl-3-[(ΔZ)-2-(4-chlorophenyl)-3,3,3-trifluoro-1-propenyl]-cyclopropane carboxylate 0.85 g of the product of Example 1 were dissolved in 3.75 ml of a normal sodium hydroxide solution and the solution was stirred for 7 hours at 40° C. Then it was poured into a mixture of water and ice and, 4 ml of a normal solution of hydrochloric acid were added, followed by washing with water and with a saturated solution of sodium chloride, drying and evaporation to dryness to obtain 0.84 g of product. The latter was dissolved with 540 mg of (R)-6-(3-phenoxy)-α-methyl-2-pyridine-methanol in 4 ml of methylene chloride. The mixture was cooled in an ice bath and a solution of 520 mg of dicyclohexylcarbodiimide, 8 mg of 4-dimethylaminopyridine and 3 ml of methylene chloride was added. The mixture was stirred for 5 minutes in the ice bath and for one night at ambient temperature. The solution was filtered, rinsed with isopropyl ether and brought to dryness to obtain 1.38 g of product which was chromatographed on silica and eluted with a hexane-isopropyl ether mixture (8–2) to obtain 1 g of the expected product with a specific rotation of $[\alpha]_D = +98° \pm 2°$ (c=1%).

EXAMPLE 4

α-Cyano-4-fluoro-3-phenoxy-benzyl [1R-[1α(S*)-3β]-2,2-dimethyl-3-[(ΔZ) 2-(4-chlorophenyl)-3,3,3-trifluoro-1-propenyl]-cyclopropane carboxylate 1.32 g of 2-(trimethylsilyl)-ethyl [1R-(1α,3β)]-2,2-dimethyl-3-[(ΔZ) 2-(4-chlorophenyl)-3,3,3-trifluoro-1-propenyl]-cyclopropane carboxylate and 6.3 ml of a molar solution of tetrabutylammonium fluoride in tetrahydrofuran were stirred for 6 hours at ambient temperature and the mixture was poured into a mixture of water and ice. 1.55 ml of a normal solution of hydrochloric acid were added After extraction with isopropyl ether, the extracts were washed with a saturated solution of sodium chloride, dried and evaporated to dryness to obtain 1.1 g of product which was added with 780 mg of (S) α-cyano-4-fluoro-3-phenoxy-benzyl alcohol to 6 ml of methylene chloride. After cooling in an ice bath, a solution of 650 mg of dicyclohexyl-carbodiimide, 10 mg of 4-dimethylamino-pyridine and 4 ml of methylene chloride were added and the mixture was stirred for 5 minutes at 0°±5° C. then for one hour at ambient temperature, followed by filtration, and rinsing with isopropyl ether to obtain 1.7 g of product. The latter was chromatographed on silica and eluted with a hexane-isopropyl ether mixture (8–2) to obtain 416 g of the expected product melting at 78° C. and having a specific rotation of $[\alpha]_D = +49° \pm 1.5°$ (c=1% in CHCl₃).

EXAMPLE 5

1-(6-phenoxy-2-pyridyl)-ethyl [1R-(1α,(RS), 3β]] 2,2-dimethyl-3-[(ΔZ)-2-(4-chlorophenyl)-3,3,3-trifluoro-1-propenyl]-cyclopropane carboxylate Using the procedure of Example 3, 1.07 g of (RS) 6-(3-phenoxy)-β-methyl-2-pyridine-methanol were reacted to obtain 3 g of product which was chromatographed on silica (eluent: hexane-isopropyl ether 9–1 to obtain 1.97 g of the expected product.

EXAMPLE 6

A homogeneous mixture was prepared from 0.25 g of the product of Example 3, 1.00 g of Piperonyl butoxide, 0.05 g of Tween 80, 0.1 g of Topanol A and 98.4 g of water.

EXAMPLE 7

Preparation of an emulsifiable concentrate

The following were vigorously mixed: 0.015 g of product of Example 4, 0.5 g of Piperonyl butoxide, 0.1 g of Topanol A, 3.5 g of Tween 80 and 95.885 g of xylene.

EXAMPLE 8

Preparation of an emulsifiable concentrate

The following homogeneous mixture was made: 1.5 g of the Product of Example 3, 20.0 g of Tween 80, 0.1 g of Topanol A and 78.4 g of xylene.

EXAMPLE 9

Preparation of a fumigant composition

The following were homogeneously mixed: 0.25 g of the Product of Example 3, 25.00 g of Tabu powder, 40.00 g of Cedar leaf powder, 33.75 g of Pinewood powder, 0.5 g of Brilliant green and 0.5 g of p-nitrophenol.

EXAMPLE 10

Examples of compositions containing 1700 g of the Product of Example 3, 40 ml of Dimethylformamide and 40 ml of Olive oil.

EXAMPLE 11

Preparation of an emulsifiable concentrate

The following were homogenized 0.015 g of the Product of Example 3, 0.5 g of Piperonyl butoxide, 0.1 g of Topanol A and 99.385 g of Xylene.

EXAMPLE 12

Preparation of an emulsifiable concentrate

The following homogeneous mixture was prepared: 1.5 g of the Product of Example 4, 20 g of Tween 80, 0.1 g of Topanol A and 78.4 g of xylene.

BIOLOGICAL STUDY

A. Study of lethal activity on the house-fly

The insects tested were four-day old female house-flies and the test was carried out by topical application of 1 µl of acetone solution on the dorsal thorax of the insects using an Arnold micromanipulator. 50 individuals per treatment were used and a mortality check was carried out 24 hours after treatment. The tests were carried out without a synergist or with the addition of piperonyl butoxide (10 parts of synergist per 1 part of test compound). The experimental results, given in the following table, are expressed in LD 50 (in nanograms) necessary to kill 50% of the insects:

| Compound of Example | LD 50 in ng/insect |
|---|---|
| 3 | 19.6 |
| 4 | 5.3 |

B. Study of the lethal effect on *Aphis cracivora*

7-day old adults were used and 10 aphids per concentration used were employed. A contact-injection method was used and the treatment of a broad-bean leaf was carried out with a Fisher gun, the leaf being placed in a plastic Petri dish on a circle of damp paper. The treatment was carried out with 2 ml of acetone solution of the product under test (1 ml per side of leaf). The infestation by the insects was brought about after drying the leaf and the insects were kept in contact with the leaf for one hour. Insects were placed on untreated leaves and the mortality was checked after 24 hours.

The experimental results obtained are given in the following table:

| Compound of Example | LC 50 in mg/l |
|---|---|
| 3 | 1.34 |
| 4 | 0.6 |

C. Study of the acaricide activity in animals (a) Study of the activity on *Boophilus microplus* larvae The substance under test was dissolved in a mixture of dimethylformamide, emulsifiers and Arcopal so as to obtain a concentrate emulsifying at 10%. This concentrate was diluted with water to obtain solutions of the desired concentrations of 100, 10 and 1 ppm. Using a spraying tower, the various solutions were sprayed over the larvae of tropical cattle ticks of *Boophilus microplus* type, and after 24 hours, the percentage of mortality was determined by counting the living and dead larvae. The results are as follows:

| | Results % of mortality Product of Example | | |
|---|---|---|---|
| Dose in ppm | 3 | 4 | 5 |
| 100 | 100 | 100 | — |
| 10 | 100 | 100 | 100 |
| 1 | 100 | 100 | 100 |

Conclusion: the product of Examples 3, 4 and 5 present a remarkable activity.

(b) Study of the activity on inhibition of the reproduction of *Boophilus microplus* ticks

*Boophilus microplus* females, ready to lay eggs, were submerged for 5 minutes in the solutions prepared above and then they were placed in a heated chamber to lay the eggs. The following were determined: (a) the percentage of ticks which did not lay eggs, (b) the quantity of eggs laid in relation to a control and (c) the percentage of larvae which hatched. The percentage of inhibition of reproduction was calculated in relation to the figures obtained; 100% indicates that inhibition was total and 0% that reproduction was identical to that obtained with the controls. The following results were obtained:

| | Results % of inhibition Product of Example | | |
|---|---|---|---|
| Dose in ppm | 3 | 4 | 5 |
| 100 | 100 | 100 | 100 |
| 50 | 100 | 100 | 100 |
| 25 | 100 | 100 | 100 |
| 12.5 | 100 | 100 | 100 |
| 6.2 | 100 | 100 | 100 |
| 3.1 | 100 | 100 | 100 |
| 1.5 | 100 | 100 | 100 |
| 0.75 | 100 | 100 | 100 |
| 0.38 | 100 | 100 | 85 |
| 0.19 | 100 | 100 | — |

Conclusion: The products of Examples 3, 4 and 5 present a remarkable activity.

Various modifications of the products and processes of the invention may be made without departing from the spirit or scope thereof and it should be understood that the invention is intended to be limited only as defined in the appended claims.

What we claim is:

1. A process for the preparation of a trifluoromethyl-vinyl compound of the formula (I) in all its possible stereoisomeric forms or mixtures thereof comprising reacting a salt of trifluoroacetic acid with a halovinyl compound of formula (II) in the presence of a cuprous salt to obtain the same stereo-specific trifluoromethylvinyl compound

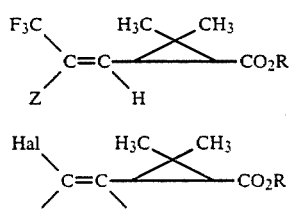

Z is an electro-attracting group, Hal is a halogen, and R is a residue of a pyrethrinoid alcohol or an acid blocking alcohol.

2. The process of claim 1 wherein the salt of acetic acid is sodium trifluoroacetate.

3. The process of claim 1 wherein the cuprous salt is cuprous iodide.

4. The process of claim 1 wherein a compound of the formula

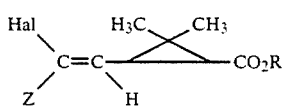

in all its possible stereoisomeric forms and mixtures thereof wherein Z is an electro-attracting group, Hal is bromine, chlorine or iodine and R is a residue of a pyrethrinoid alcohol or of an acid blocking alcohol is reacted with sodium trifluoroacetate in the presence of cuprous iodide to obtain a compound of the formula:

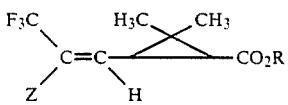

5. The process of claim 4 wherein Hal is bromine.

6. The process of claim 4 wherein Z is aryl or haloaryl.

7. The process of claim 4 wherein Z is phenyl or 4-chlorophenyl.

8. The process of claim 4 wherein Z is —COOR' and R' is unsubstituted or substituted alkyl of 1 to 8 carbon atoms.

9. The process of claim 4 wherein R is selected from the group consisting of alkyl of 1 to 8 carbon atoms, trialkylsilyl alkyl of 1 to 8 carbon atoms, benzyl and benzyl substituted with at least one member of the group consisting of alkyl of 1 to 4 carbon atoms, alkenyl and alkenyloxy of 2 to 6 carbon atoms, alkadienyl of 4 to 8 carbon atoms, halogen and methylenedioxy.

10. The process of claim 4 wherein R is alkyl of 1 to 4 carbon atoms.

11. The process of claim 4 wherein R is trimethylsilyl alkyl of 1 to 4 carbon atoms.

12. The process of claim 4 wherein R is selected from the group consisting of (a) a group of the formula

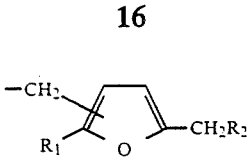

wherein $R_1$ is hydrogen or methyl and $R_2$ is monocyclic aryl or —CH≡CH, (b) or a group

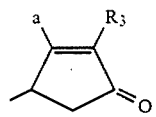

in which a is hydrogen or methyl and $R_3$ is an aliphatic organic of 2 to 6 carbon atoms having one or more carbon-carbon unsaturations, (c) or a group

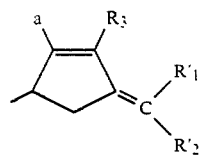

in which a is hydrogen or methyl, $R_3$ has the above definition, $R'_1$ and $R'_2$ are individually hydrogen, halogen, alkyl of 1 to 6 carbon atoms, aryl of 6 to 10 carbon atoms, alkoxycarbonyl of 2 to 5 carbon atoms, or cyano, (d) or a group

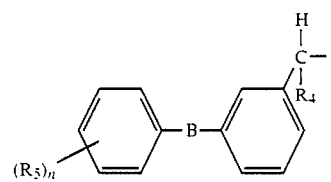

in which B is oxygen or sulfur,

or —CH$_2$— or a sulfoxide or a sulfone and $R_4$ is hydrogen, —C≡N, methyl, —CONH$_2$, —CSNH$_2$ or —C≡CH, $R_5$ is halogen or methyl and n is 0, 1 or 2, (e) or a group

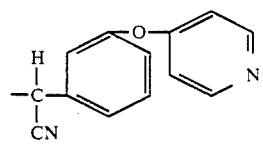

(f) or a group

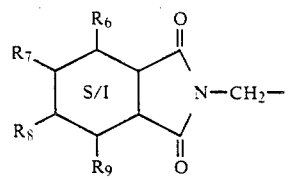

in which $R_6$, $R_7$, $R_8$, $R_9$ are hydrogen, chlorine, or methyl and which S/I symbolizes an aromatic ring or a dihydro or tetrahydro ring, (g) or a group

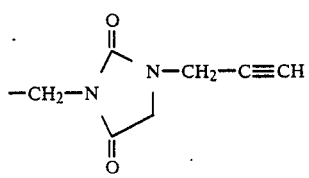

(h) or a group

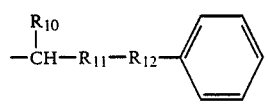

in which $R_{10}$ is hydrogen or —CN, $R_{12}$ is —CH$_2$— or oxygen, $R_{11}$ is thiazolediyl or thiadiazolediyl in which the bond with
can be found in any of the positions available, $R_{12}$ is linked to $R_{11}$ by the carbon contained between the sulfur atom and the nitrogen, (i) or a group

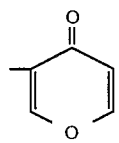

(j) or a group

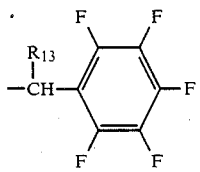

in which $R_{13}$ is hydrogen or CN, (k) or a group

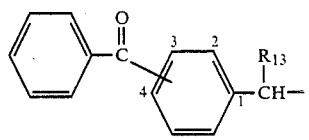

in which $R_{13}$ is defined as above, and the benzoyl radical is in position 3 or 4, (l) or a group

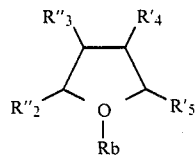

in which one of $R_2''$ or $R_3''$ is

Z is hydrogen, C≡N, C≡CH, CF$_3$ or alkyl of 1 to 3 carbon atoms and the other $R_2''$ or $R_3''$ and $R_4'$ and $R_5'$ are individually hydrogen, halogen, alkyl of 1 to 18 carbon atoms, aryl of 6 to 14 carbon atoms, arylalkyl of 7 to 18 carbon atoms, cyano, —CF$_3$, alkoxycarbonyl of 2 to 8 carbon atoms, —NO$_2$, alkyloxy of 1 to 8 carbon atoms.

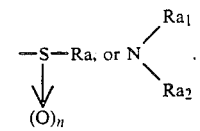

n being 0, 1 or 2 and the radicals Ra, Ra$_1$ and Ra$_2$ are alkyl of 1 to 8 carbon atoms, Rb is either

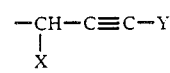

in which X and Y are individually hydrogen, halogen, alkyl of 1 to 8 carbon atoms or aryl of 6 to 14 carbon atoms or

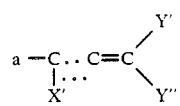

radical in which X', Y' and Y" are individually one of values indicated above for X and Y, the dotted line representing a possible double bond between the carbons 1 and 2; (m) or

in which r' can have the values indicated previously for $R_4'$ and $R_5'$ with the exception of halogen, cyano, —NO$_2$,

in which n is either 1 or 2 and

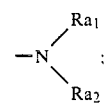

(n) or

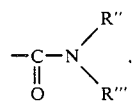

, in which R" and R''' are individually hydrogen alkyl of 1 to 18 carbon atoms, aryl of 6 to 14 carbon atoms, aralkyl of 7 to 18 carbon atoms, CF$_3$, alkoxycarbonyl of 2 to 8 carbon atoms or alkoxy of 1 to 8 carbon atoms, (o) or a group

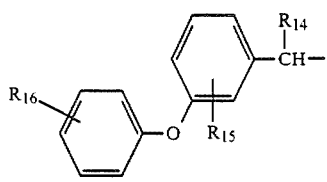

in which $R_{14}$ is hydrogen, methyl, ethynyl or cyano and $R_{15}$ and $R_{16}$ are individually hydrogen, fluorine or bromine, (p) or a group

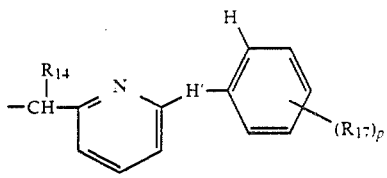

in which $R_{14}$ is defined as above, each of the $R_{17}$'s independently is alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo, p is an integer 0, 1 or 2 and B' is oxygen or sulfur.

13. A process of claim 1 wherein the final product is selected from the group consisting of methyl [1R-(1α, 3β) 2,2-dimethyl-3-[(ΔZ)-2-(4-chlorophenyl)-3,3,3-trifluoro-1-propenyl]cyclopropane carboxylate and 2-(trimethylsilyl)-ethyl [1R-(1α, 3β) 2,2-dimethyl- [-3-[(ΔZ)-2-(4-chlorophenyl)-3,3,3-trifluoro-1-propenyl]-cyclopropane carboxylate.

* * * * *